United States Patent
Wen et al.

(10) Patent No.: US 11,313,734 B2
(45) Date of Patent: Apr. 26, 2022

(54) FLEXIBLE TEMPERATURE SENSOR

(71) Applicant: WUYI UNIVERSITY, Jiangmen (CN)

(72) Inventors: Jinxiu Wen, Jiangmen (CN); Jianyi Luo, Jiangmen (CN); Baowen Liang, Jiangmen (CN); Xiaoyan Hu, Jiangmen (CN); Jingcheng Huang, Jiangmen (CN); Zhundong Li, Jiangmen (CN)

(73) Assignee: Wuyi University, Jiangmen (CN)

( * ) Notice: Subject to any disclaimer, the term of this patent is extended or adjusted under 35 U.S.C. 154(b) by 198 days.

(21) Appl. No.: 16/646,748

(22) PCT Filed: Feb. 13, 2019

(86) PCT No.: PCT/CN2019/074948
§ 371 (c)(1),
(2) Date: Mar. 12, 2020

(87) PCT Pub. No.: WO2020/155195
PCT Pub. Date: Aug. 6, 2020

(65) Prior Publication Data
US 2021/0131877 A1    May 6, 2021

(30) Foreign Application Priority Data
Feb. 2, 2019   (CN) .......................... 201910107784.0

(51) Int. Cl.
*G01K 7/22*     (2006.01)
*D01B 1/14*     (2006.01)
(Continued)

(52) U.S. Cl.
CPC ................ *G01K 7/22* (2013.01); *D03D 1/00* (2013.01); *D04B 1/14* (2013.01); *G01K 7/18* (2013.01);
(Continued)

(58) Field of Classification Search
CPC ... G01K 7/22; G01K 7/18; D03D 1/00; D04B 1/14; A61B 5/6804; D10B 2101/12; D10B 2401/16
See application file for complete search history.

(56) References Cited

U.S. PATENT DOCUMENTS 4,795,998 A * 1/1989 Dunbar ................ H01H 13/785
338/5
4,921,751 A    5/1990 Wakahara et al.
(Continued)

FOREIGN PATENT DOCUMENTS

CN    101561324 A    10/2009
CN    106211383 A    12/2016
(Continued)

OTHER PUBLICATIONS

English Machine Translation of CN107043990A to Li et al.; Aug. 15, 2017 (Year: 2017).*

(Continued)

*Primary Examiner* — Nathaniel T Woodward
*Assistant Examiner* — Philip L Cotey
(74) *Attorney, Agent, or Firm* — Vivacqua Crane PLLC

(57) ABSTRACT

Provided is a flexible temperature sensor including a flexible temperature-sensing fabric, wherein the flexible temperature-sensing fabric includes a fabric base and at least one flexible temperature-sensing conductive fiber, the fabric base is a flat fabric woven from a plurality of insulating fibers, and the temperature-sensing conductive fiber is fixed in the fabric base by weaving. The flexible temperature sensor has the advantages of being easy to fabricate, low in cost, washable, wide in temperature monitoring range, high in sensitivity, good in stability and repeatability, and compatible with existing textile technologies.

6 Claims, 4 Drawing Sheets

(51) Int. Cl.
  *D04B 1/14* (2006.01)
  *G01K 7/18* (2006.01)
  *D03D 1/00* (2006.01)
  *A61B 5/00* (2006.01)

(52) U.S. Cl.
  CPC ........ *A61B 5/6804* (2013.01); *D10B 2101/12* (2013.01); *D10B 2401/16* (2013.01)

(56) References Cited

U.S. PATENT DOCUMENTS

| | | | | |
|---|---|---|---|---|
| 5,422,462 | A * | 6/1995 | Kishimoto | H05B 1/0272 219/529 |
| 6,713,733 | B2 * | 3/2004 | Kochman | H05B 3/58 219/494 |
| 9,603,560 | B2 * | 3/2017 | Monty | A61B 10/0064 |
| 2003/0189037 | A1 * | 10/2003 | Kochman | H05B 3/58 219/549 |
| 2004/0056753 | A1 * | 3/2004 | Chiang | G01K 3/14 338/22 R |
| 2005/0061801 | A1 * | 3/2005 | Kuo | H05B 3/347 219/529 |
| 2013/0020313 | A1 * | 1/2013 | Swallow | D03D 1/0088 219/545 |
| 2013/0203201 | A1 * | 8/2013 | Britton | H01C 7/04 438/54 |
| 2015/0250420 | A1 * | 9/2015 | Longinotti-Buitoni | A61B 5/1135 600/301 |
| 2017/0224280 | A1 * | 8/2017 | Bozkurt | A61B 5/282 |
| 2017/0233902 | A1 * | 8/2017 | Grant | G01K 13/00 139/425 A |
| 2018/0171514 | A1 * | 6/2018 | Cobanoglu | D03D 11/00 |
| 2019/0072440 | A1 * | 3/2019 | Menon | D03D 1/0088 |
| 2019/0132948 | A1 * | 5/2019 | Longinotti-Buitoni | A61B 5/7278 |
| 2019/0297961 | A1 * | 10/2019 | Strecker | A41D 1/005 |
| 2019/0353533 | A1 * | 11/2019 | Marchesi | D04B 21/14 |
| 2020/0044136 | A1 * | 2/2020 | Zhang | H01L 35/34 |

FOREIGN PATENT DOCUMENTS

| | | |
|---|---|---|
| CN | 107022823 A | 8/2017 |
| CN | 107043990 A | 8/2017 |
| CN | 107242856 A | 10/2017 |
| JP | 2012-197521 A | 10/2012 |

OTHER PUBLICATIONS

Chun-Chih Huang "Flexible Miniaturized Nickel Oxide Thermistor Arrays via Inkjet Printing Technology"; Applied Materials & Interfaces; ACS Appl. Mater. Interfaces 2013, 5, 12954-12959.

Chaoyi Yan "Highly Stretchable Piezoresistive Graphene-Nanocellulose Nanopaper for Strain Sensors"; Adv. Mater. 2014, 26, 2022-2027.

Wataru Honda "Wearable, Human-Interactive, Health-Monitoring, Wireless Devices Fabricated by Macroscale Printing Techniques"; Adv. Funct. Mater. 2014, 24, 3299-3304.

Chai Chunpeng & Li Guoping, Polymeric Synthetic Materials, Jan. 2019, p. 159-163, First Edition, Beijing Institute of Technology Press., China.

* cited by examiner

FLEXIBLE TEMPERATURE SENSOR

CROSS-REFERENCE TO RELATED APPLICATIONS

This application claims priority to PCT Application No. PCT/CN2019/074948 filed on Feb. 13, 2019, which claims priority to Chinese Patent Application No. 201910107784.0 filed on Feb. 2, 2019, the entire contents both of which are hereby incorporated by reference.

FIELD OF TECHNOLOGY

The following relates to the technical field of sensors, in particular to a flexible temperature sensor.

BACKGROUND

Temperature is closely related to physical, chemical, biological, environmental and electronic systems and is one of the highly-focused parameters. At present, sensors used for temperature detection typically include thermocouple and resistance temperature sensors, and infrared and semiconductor temperature sensors, wherein resistance temperature sensors made from platinum (Pt) are mostly widely used on the market and have the most stable performance; however, such temperature sensors are inflexible and poor in biological compatibility. Particularly, temperature sensors used for temperature measurement of electronic skin, robot sensors, environmental safety and human health are generally required to have the characteristics of simple operation, low weight, biocompatibility, high sensitivity, high flexibility, and the like. Therefore, flexible temperature sensors have become one of the research focuses at home and abroad.

In recent years, several technical solutions to flexible temperature sensors have been reported and provided such as the temperature sensor, put forward by Liao Ying-Chih et al., from Taiwan, adopting a nickel-oxide film thermistor array printed on a polyimide substrate through an ink-jet printing process to realize temperature sensing; the flexible sensor, put forward by Takei Kuniharu et al., from Japan, synthesized by modification of a polydimethylsiloxane (PDMS) and PEDOT:PSS polymer with carbon nano-tubes and applied to stress and temperature monitoring; and the stretchable graphene thermistor temperature sensor, put forward by Lee Pooi See et al., from Singapore, prepared on a PDMS polymer through planography. However, all these flexible temperature sensors have great limitations in actual use. For example, the uniformity of carbon nano-materials used for modification may affect the measurement precision of the temperature sensor; a polymer substrate may deform with the increase of temperature, which in turn leads to poor temperature measurement stability, a narrow measurement range, a complex preparation process, and poor experience when the sensor is worn on a human body.

To further satisfy the pursuit of people for smart clothing, wearable electronic fabrics have emerged. Most existing temperature sensors are manufactured by adopting a substrate made from a clothing fabric and having the surface loaded with conductive materials. Such temperature sensors are compatible with fabrics, but have the problems of harsh tactile feeling of fabrics loaded with metal or carbon conductive materials, poor comfort, complex preparation process, and poor uniformity and stability of the materials loaded on the fabrics.

Therefore, it will be of great significance in the fields of smart wearable devices and electronic fabric to invent a flexible temperature sensor which is soft, comfortable, washable, high in sensitivity, good in stability and repeatability, and wide in temperature detection range.

SUMMARY

An aspect relates to a flexible temperature sensor which has the advantages of being easy to fabricate, low in cost, washable, wide in temperature monitoring range, high in sensitivity, good in stability and repeatability, and compatible with existing textile technologies.

The technical solution adopted by embodiments of the invention is as follows:

A flexible temperature sensor includes a flexible temperature-sensing fabric, wherein the flexible temperature-sensing fabric includes a fabric base and at least one flexible temperature-sensing conductive fiber, the fabric base is a flat fabric woven from a plurality of insulating fibers, and the temperature-sensing conductive fiber is fixed in the fabric base by weaving.

According to the flexible temperature sensor of embodiments of the invention, the temperature-sensing conductive fiber is used as a temperature-sensing element and is woven into the fabric base, so that the sensor is easy to manufacture, low in manufacturing cost, and compatible with existing textile technologies; the temperature-sensing conductive fiber can be woven into a clothing fabric or a wearable article, so that the functions and attributes of the fabric are maintained, wear comfort is guaranteed, the weight is low, and the body temperature can be monitored in real time. Tests prove that the flexible temperature sensor of embodiments of the invention has the advantages of being washable, wide in temperature monitoring range, high in sensitivity, and good in stability and repeatability.

Furthermore, the temperature-sensing conductive fiber is a carbon fiber doped with impurity ions.

In embodiments of the invention, a primary fiber is subjected to ion doping (ion doping means that impurity ions are inevitably brought into the material, or more impurity ions are mixed into the material through extra doping), then the primary fiber is placed into an oxidization furnace to be oxidized and is finally carbonized in a carbonization furnace at a high temperature to obtain an impurity ion-doped carbon fiber which is used as the temperature-sensing conductive fiber, and then the temperature-sensing conductive fiber is woven with common insulating fibers to prepare the flexible temperature-sensing fabric. The impurity ions uniformly distributed in the temperature-sensing conductive fiber are ionized at the indoor temperature to form a positive or negative electric center which generates a local electric field near the impurity ions, so that the moving direction and speed of current carriers passing near the impurity center will be changed under the effect of a Coulomb attraction or repulsive force, and this process is referred to as impurity scattering. The impurity scattering is affected by temperature. Particularly, with the increase of temperature, the impurity scattering will become weak, the migration rate of the current carriers will increase accordingly, and macroscopically, the resistance of the temperature-sensing conductive fiber is decreased and is in negative correlation with the variation trend of temperature.

The carbon fiber doped with impurity ions is used as the temperature-sensing conductive fiber, so that the preparation process is simple; and the temperature-sensing conductive fiber prepared through ion doping and high-temperature carbonization realizes the temperature-sensing characteristic without surface modification with other materials, so that the temperature measurement precision will not be limited by the uniformity of modification materials, and the obtained temperature-sensing conductive fiber is wide in temperature detection range, high in sensitivity, and good in stability and repeatability.

Furthermore, the resistance of the temperature-sensing conductive fiber is characterized by a negative temperature coefficient, and the resistance between two ends of the temperature-sensing conductive fiber decreases with the increase of temperature.

Furthermore, the temperature-sensing conductive fiber is free of cross or contact parts, so that short circuits are avoided.

Furthermore, the flexible temperature sensor further includes a data acquisition element, and the two ends of the temperature-sensing conductive fiber are electrically connected to the data acquisition element respectively.

Furthermore, two terminal electrodes are separately arranged at the two ends of the temperature-sensing conductive fiber and are electrically connected to the data acquisition element through wires.

Furthermore, the flexible temperature sensor further includes a packaging housing, and the flexible temperature-sensing fabric is packaged in the packaging housing.

Furthermore, the packaging housing is made from a high-molecular polymer.

For the sake of a better understanding and implementation, embodiments of the invention is expounded below with reference to accompanying drawings.

BRIEF DESCRIPTION OF THE DRAWINGS

Some of the embodiments will be described in detail, with reference to the following figures, wherein like designations denote like members, wherein.

REFERENCE SIGNS 1, temperature-sensing conductive fiber; 2, fabric base; 3, weld point of temperature-sensing conductive fiber and wire; 4, wire; 5, packaging housing; 6, data acquisition element.

DETAILED DESCRIPTION

Figure 1:
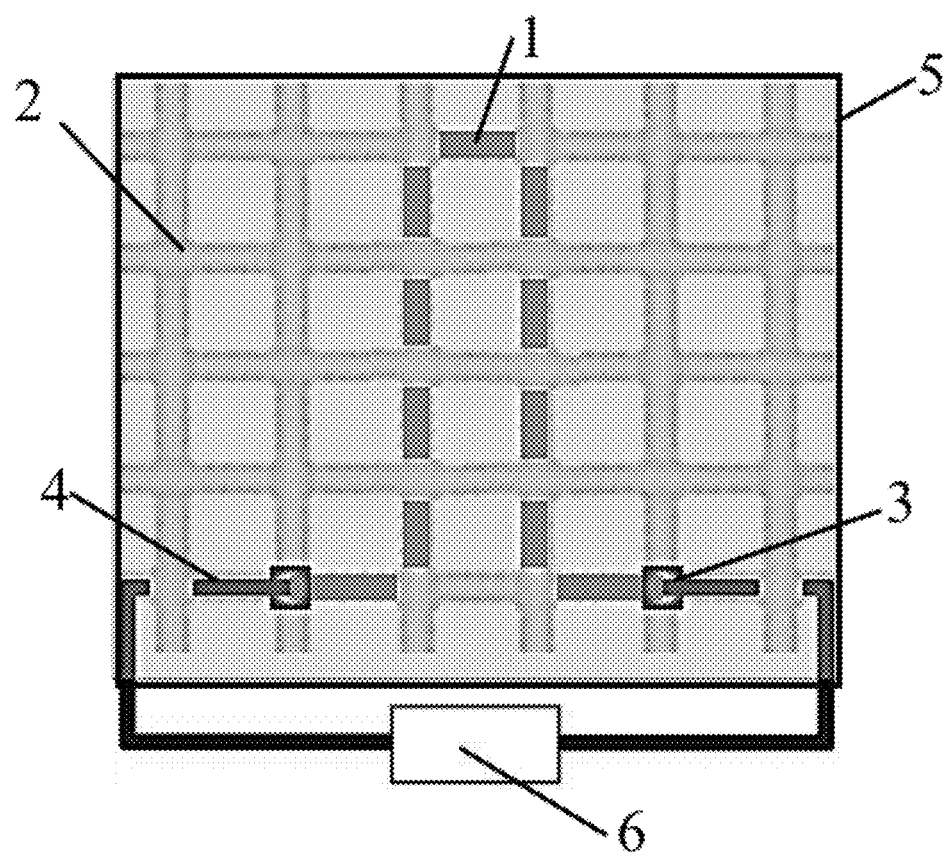
FIG. 1 is a structural view of a flexible temperature sensor of embodiments of the invention.
Figure 2:
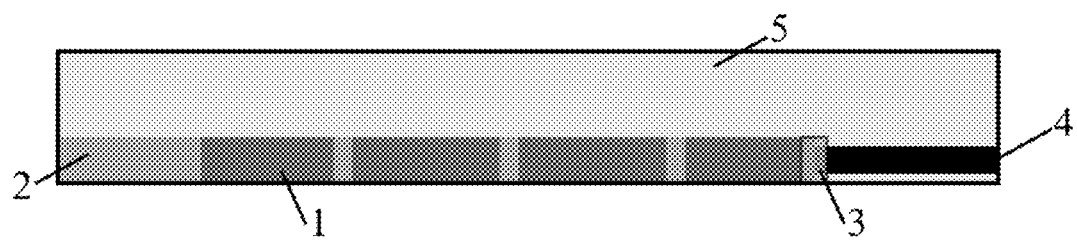
FIG. 2 is a side view of the flexible temperature sensor of embodiments of the invention.
Figure 3:
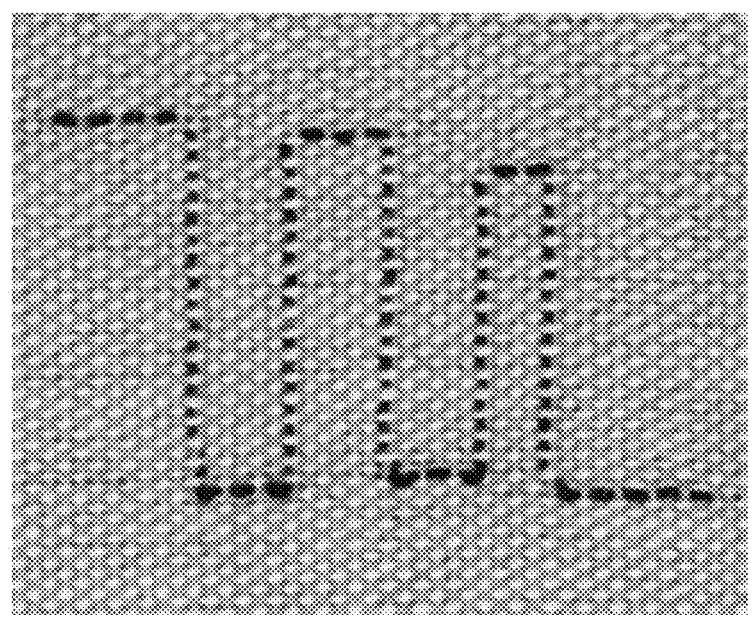
FIG. 3 is a picture of a flexible temperature-sensing fabric of embodiments of the invention.

Referring to FIG. 1-FIG. 3, the flexible temperature sensor of the invention includes a flexible temperature-sensing fabric, wherein the flexible temperature-sensing fabric includes a fabric base 2 and at least one flexible temperature-sensing conductive fiber 1, the fabric base 2 is a flat fabric woven from a plurality of insulating fibers, and the temperature-sensing conductive fiber 1 is fixed by weaving in the fabric base 2.

Furthermore, the temperature-sensing conductive fiber 1 is a carbon fiber doped with impurity ions, and the resistance of the temperature-sensing conductive fiber 1 is particularly characterized by a negative temperature coefficient. Specifically, the impurity ions doped in the temperature-sensing conductive fiber may be one or more of sodium ions, potassium ions, calcium ions, chloride ions, etc.

The temperature-sensing conductive fiber 1 is free of crossed or contact parts, so that short circuits are avoided.

Furthermore, the insulating fibers are conventional textile fibers such as polyester fibers or flax fibers.

In order to realize acquisition of detection data, the flexible temperature sensor further includes a data acquisition element 6, wherein the two ends of the temperature-sensing conductive fiber 1 are electrically connected to the data acquisition element 6 respectively. The data acquisition element 6 acquires an electrical signal by a constant voltage source and a single-chip microcomputer, then the electrical signal is converted into a temperature value according to a temperature curve formula, and the temperature value is transmitted to a terminal to be directly displayed. Two terminal electrodes are arranged respectively at the two ends of the temperature-sensing conductive fiber 1, are electrically connected to the data acquisition element 6 through wires 4 respectively, and are welded to the wires 4, and weld points 3 are shown in FIG. 1 and FIG. 2.

In order to protect the flexible temperature-sensing fabric, the flexible temperature sensor further includes a packaging housing 5, and the flexible temperature-sensing fabric is packaged inside the packaging housing, as shown in FIG. 1 and FIG. 2. Furthermore, the packaging housing 5 is made from a high-molecular polymer. The packaging housing 5 is transparent or semi-transparent. For the sake of a clearer display of the relation between the packaging housing 5 and other components, the contour of the packaging housing 5 is drawn with a blank full line in FIG. 1 and FIG. 2.

Embodiment 1

In this embodiment, sodium ions are doped into a chemical fiber precursor, and then the chemical fiber precursor is oxidized and carbonized at a high temperature to obtain a sodium ion-doped carbon fiber used as the temperature-sensing conductive fiber 1; afterwards, terminal electrodes are made by electroplating copper at the two ends of the temperature-sensing conductive fiber 1 and then are respectively welded to silver wires 4; and finally, the temperature-sensing conductive fiber 1 welded to the wires 4 is woven with polyesters to obtain a flat flexible temperature-sensing fabric, wherein the fiber in a dark color in FIG. 3 is the temperature-sensing conductive fiber 1.

Figure 4:
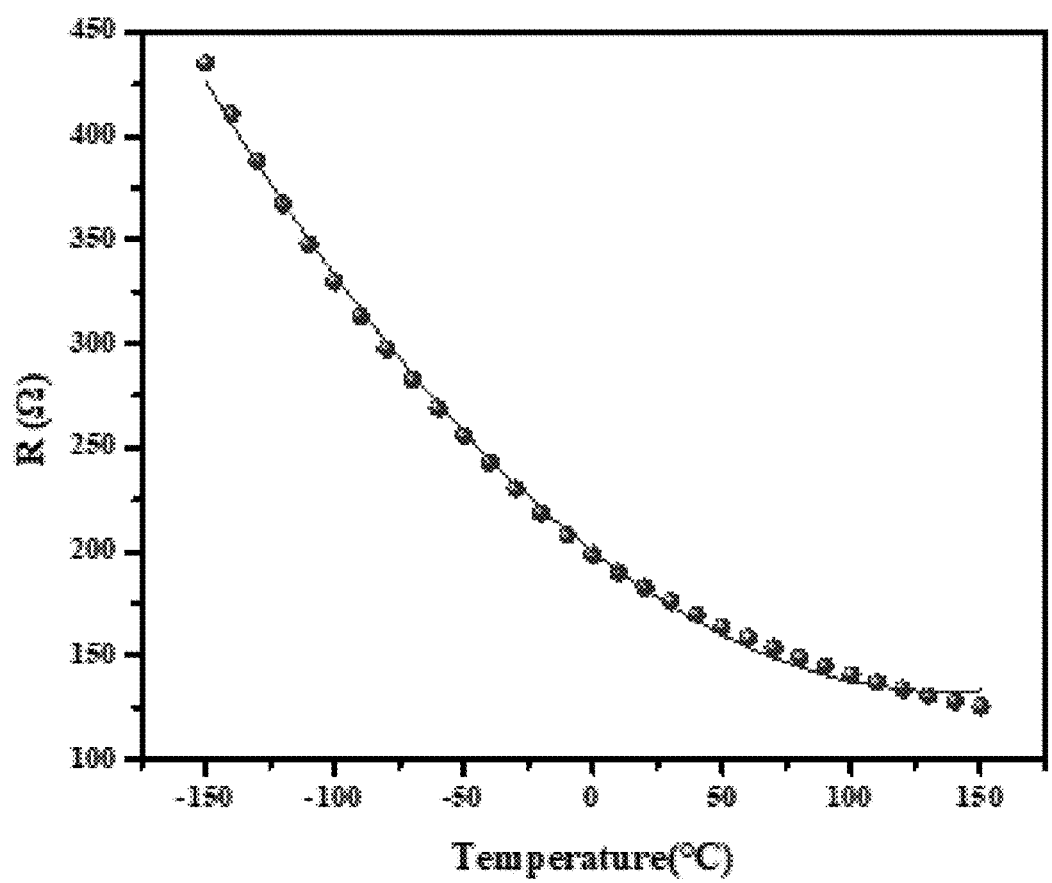
FIG. 4 is a chart of a temperature response range curve of the flexible temperature sensor of embodiments of the invention.

Afterwards, the flexible temperature-sensing fabric is packaged with a high-molecular polymer to manufacture a packaging housing 5, so that the flexible temperature sensor is obtained; then, the flexible temperature sensor is placed on a variable-temperature stand to test a temperature response range curve of the flexible temperature sensor. As can be seen from FIG. 4 which is a chart of the temperature response range curve of the flexible temperature sensor of embodiments of the invention, the flexible temperature sensor of embodiments of the invention is of a negative temperature coefficient type, that is, the resistance of the flexible temperature sensor decreases with the increase of temperature. In addition, the flexible temperature sensor of embodiments of the invention can detect temperatures ranging from −150° C. to 150° C., and the temperature response curve of the flexible temperature sensor matches a quadratic function fitting curve, which means that the flexible temperature sensor of embodiments of the invention has a wide temperature detection range.

Embodiment 2

Figure 5:
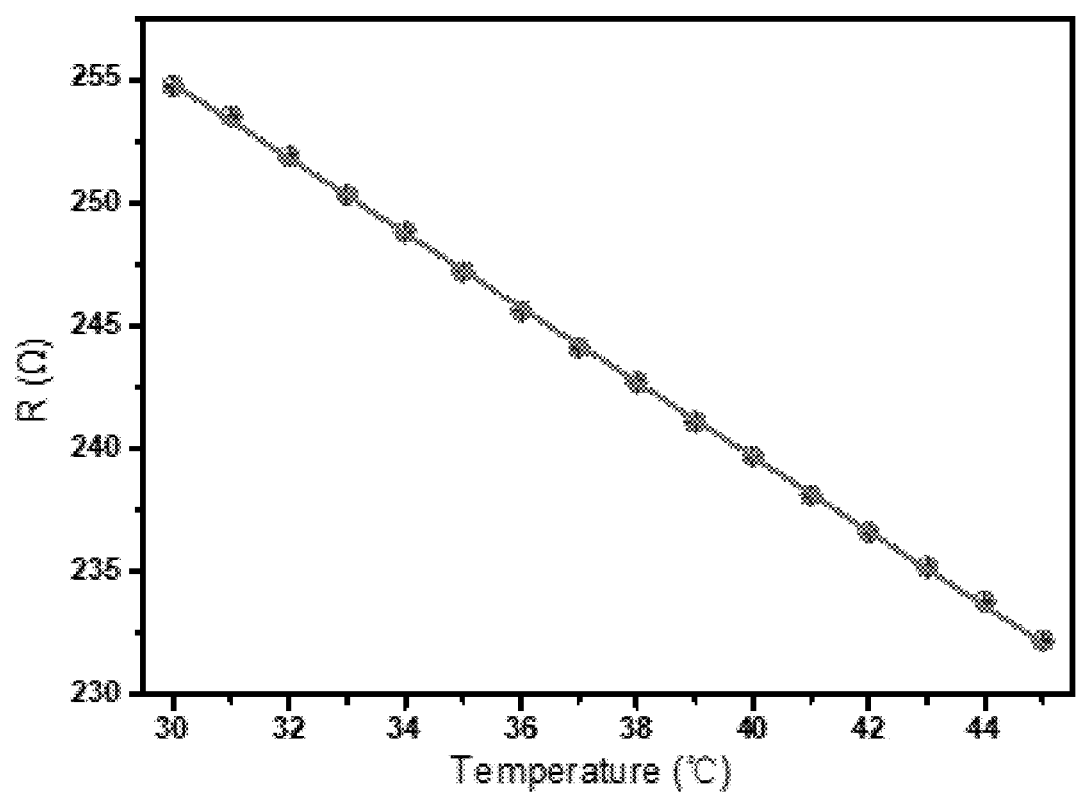
FIG. 5 is a chart of a temperature response curve of the flexible temperature sensor within the body temperature range (30° C.-45° C.) of embodiments of the invention.

The flexible temperature sensor is prepared through the method in Embodiment 1 and is then placed on the variable-temperature stand to detect the temperature response of the sensor within the body temperature variation range, wherein the detection range is 30° C.-45° C., and the temperature interval is 1° C., and an obtained temperature response curve is shown in FIG. 5. As can be seen from FIG. 5, the flexible temperature sensor of embodiments of the invention has good sensitivity, the resistance variation of the sensor is in a good linear relation with the temperature variation within 30° C.-45° C., and thus, the flexible temperature sensor can monitor the body temperature in real time.

Embodiment 3

Figure 6:
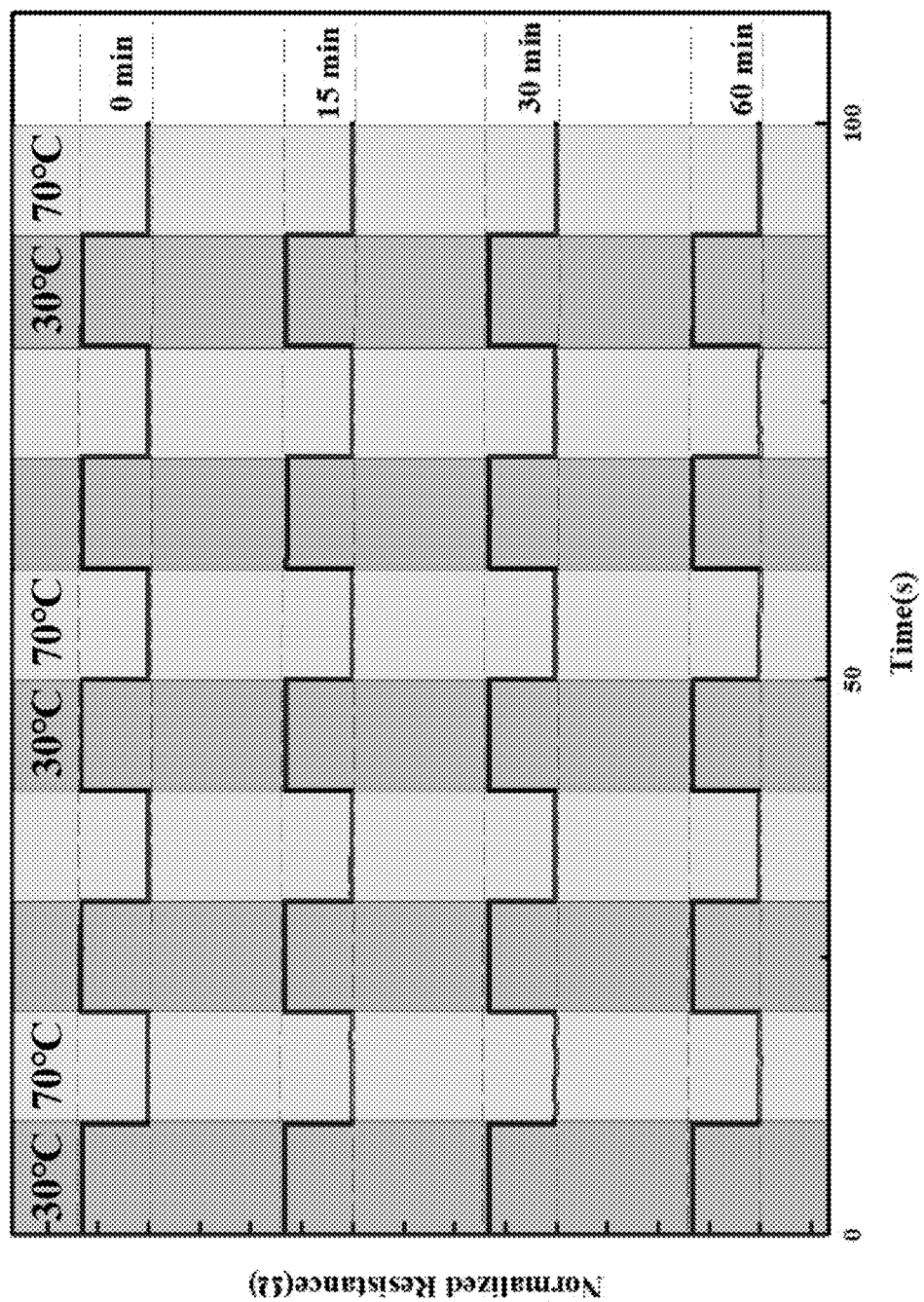
FIG. 6 is a chart of a temperature response curve of the flexible temperature sensor after the temperature sensor is washed for different times and dried in embodiments of the invention.

The flexible temperature sensor is prepared through the method in Embodiment 1, is then placed in water to be ultrasonically cleaned for different times after the packaging housing 5 is removed, and then is dried to test the temperature response performance of the sensor at the temperature of 30° C. and the temperature of 70° C. As shown in FIG. 6, the test result indicates that the repeatability of the temperature response of the sensor is good after the sensor is ultrasonically cleaned for as long as 60 minutes, which fully proves that the flexible temperature sensor of embodiments of the invention is washable and is stable in temperature response.

Although the invention has been illustrated and described in greater detail with reference to the preferred exemplary embodiment, the invention is not limited to the examples disclosed, and further variations can be inferred by a person skilled in the art, without departing from the scope of protection of the invention.

For the sake of clarity, it is to be understood that the use of "a" or "an" throughout this application does not exclude a plurality, and "comprising" does not exclude other steps or elements.

What is claimed:

1. A flexible temperature sensor, comprising a flexible temperature-sensing fabric, wherein the flexible temperature-sensing fabric comprises a fabric base and at least one flexible temperature-sensing conductive fiber; the fabric base is a flat fabric woven from a plurality of insulating fibers, and the temperature-sensing conductive fiber is fixed in the fabric base in a woven manner, wherein the temperature-sensing conductive fiber is a carbon fiber doped with impurity ions, the resistance of the temperature-sensing conductive fiber has a negative temperature coefficient characteristic, and the impurity ions doped in the temperature-sensing conductive fiber include one or more of sodium ions, potassium ions, calcium ions, and chloride ions.

2. The flexible temperature sensor of claim 1, wherein the temperature-sensing conductive fiber has no cross or contact parts.

3. The flexible temperature sensor of claim 1, further comprising a data acquisition element, and two ends of the temperature-sensing conductive fiber are electrically connected to the data acquisition element respectively.

4. The flexible temperature sensor of claim 3, wherein the two ends of the temperature-sensing conductive fiber each have an end terminal electrode, and the terminal electrodes are electrically connected to the data acquisition element through wires.

5. The flexible temperature sensor of claim 1, further comprising a packaging housing, and the flexible temperature-sensing fabric is packaged in the packaging housing.

6. The flexible temperature sensor of claim 5, wherein the packaging housing is made of high-molecular polymer.

* * * * *